United States Patent [19]

Stearns et al.

[11] Patent Number: 5,541,519

[45] Date of Patent: Jul. 30, 1996

[54] PHOTOIONIZATION DETECTOR INCORPORATING A DOPANT AND CARRIER GAS FLOW

[76] Inventors: Stanley D. Stearns, 1201 Archley St., Houston, Tex. 77055; Wayne E. Wentworth, 614 E. Larkspur Cir., Pearland, Tex. 77584

[21] Appl. No.: 349,039

[22] Filed: Dec. 2, 1994

Related U.S. Application Data

[63] Continuation-in-part of Ser. No. 662,149, Feb. 28, 1991, Pat. No. 5,153,519, and a continuation-in-part of Ser. No. 956,632, Oct. 5, 1992, Pat. No. 5,317,271, and a continuation-in-part of Ser. No. 176,968, Jan. 3, 1994, Pat. No. 5,394,092, and a continuation-in-part of Ser. No. 201,467, Feb. 25, 1994, Pat. No. 5,394,090, and a continuation-in-part of Ser. No. 201,469, Feb. 25, 1994, Pat. No. 5,394,091.

[51] Int. Cl.$^6$ .......................... G01N 27/62; G01N 27/68
[52] U.S. Cl. .......................... 324/464; 324/455; 73/28.02
[58] Field of Search .................................. 324/449, 450, 324/452, 455, 464, 123 R, 71.4; 73/28.02; 250/379, 385; 313/231.41, 231.71; 315/111.01, 111.91; 436/153

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |
| 5,338,931 | 8/1994 | Spangler et al. | 250/287 |
| 5,394,090 | 2/1995 | Wentworth et al. | 324/464 |
| 5,394,091 | 2/1995 | Wentworth et al. | 324/464 |
| 5,394,092 | 2/1995 | Wentworth et al. | 324/464 |

OTHER PUBLICATIONS

A Compilation of Research on Pulsed Discharge Detectors, Article, Summary of Paper Presented at the Pittsburgh Conference, 1994.

Introduction to: Pulsed Discharge Helium Ionization Detector, Reprint of Publication in the Journal of Chromatographia, vol. 34, No. 5–8, pp. 219–115 (1992).

Introduction to: Pulsed Discharge Electron Capture Detector Reprint devoted soley to the PDECD (J of Chromatogra. Sci.,vol. 30, pp. 478–485, (1992).

Pulsed Discharge Helium Ionization Detector, W. E. Wentworth, S. V. Vasnin, Stearns, & Meyer, Chromatographia, vol. 34, No. 5–8, Sep./Oct. 1992.

Pulsed Discharge Photoionization Detector (PDPID), A Summary of a paper presented at the 1994—Pittsburgh Conference by W. E. Wentworth.

Pulsed Discharge Emission Detector–Application to Analytical Spectroscopy of Permanent Gases, Vasnin, Wentworth, Stearns & Meyer, Chromatographia, vol. 34, No. 5–8, Sep./Oct. 1992.

(List continued on next page.)

Primary Examiner—Kenneth A. Wieder
Assistant Examiner—Diep Do
Attorney, Agent, or Firm—Gunn & Associates, P.C.

[57] ABSTRACT

A pulsed rare gas photoionization detector apparatus is set forth and incorporates a closed chamber for receiving a carrier gas flowing there through between inlets and outlets, and the carrier gas is exposed to a pair of electrodes forming a spark across the chamber and through the carrier gas. One component of the carrier gas is a dopant which selected from a plurality of rare gases. The sample to be analyzed is injected into the closed chamber where it commingles with the carrier gas. One reaction involves the formation of selected dopant in an excited state, which upon decay, serves as a source of ionizing radiation which reacts with sample compounds producing detectable events. These events are used to identify and quantify unknown compounds contained in the sample. The methods and apparatus are especially useful in selectively ionizing the compounds to be measured while not ionizing other constituents of the sample. This greatly enhances the signal-to-noise ratio for detecting impurity compounds. As an example, when the detection system is used to monitor air quality, the major constituents of air are not ionized.

21 Claims, 2 Drawing Sheets

OTHER PUBLICATIONS

Pulsed Discharge Helium Ionization Detector, A Universal Detector for Inorganic and Organic Compounds at the Subpicogram Level, Wentworth, et al, Version of 5/25.

Reprinted from Process Control & Quality, 5 (1993) 193–204, Elsevier Science B. V.,Amsterdam, Pulsed–Discharge Helium Ionization/Electron Capture/Emission Detector of Chlorinated Compounds, Wentworth, et al.

Environmental Applications of the Pulsed–Discharge Electron–Capture Detector, Wentworth, D'Sa & Cai, Journal of Chromatographic Science, vol. 30, Dec. 1992.

Introduction to: Pulsed Discharge Emission Detector (PDED) Chromatographia, vol. 34, pp. 226–234, (1992).

PHOTOIONIZATION DETECTOR INCORPORATING A DOPANT AND CARRIER GAS FLOW

This disclosure is a continuation in part of application Ser. No. 662,149 which was filed on Feb. 28, 1991 and which issued as U.S. Pat. No. 5,153,519 on Oct. 6, 1992, also application Ser. No. 956,632 which was filed on Oct. 5, 1992, now issued as U.S. Pat. No. 5,317,271 on May 31, 1994, application Ser. No. 176,968 which was filed on Jan. 3, 1994, now U.S. Pat. No. 5,394,092 and also application Ser. No. 201,467 filed Feb. 25, 1994, now U.S. Pat. No. 5,394,090 and application Ser. No. 201,469 filed Feb. 28, 1994, now U.S. Pat. No. 5,394,091, both filed Feb. 25, 1994.

BACKGROUND OF THE DISCLOSURE

The present disclosure involves the quantitative analysis of gases for compounds of interest and is an extension of the apparatus and methods taught in U.S. Pat. No. 5,153,519. More specifically, the invention is directed, although not limited, to the classification and quantification of impurities in air.

The referenced patent discloses the creation of several charged species by a pulsed direct current (DC) spark discharge acting on a carrier gas containing other compounds to be identified and quantified. The carrier gas is preferably an inert gas and is typically helium. The charged species are used to classify and/or quantify the unknown compounds in the carrier. This detector is connected with upstream or downstream devices such as a sample source, gas chromatograph (GC) column, spectrum analyzer or the like. A sample to be analyzed is loaded for flow along with the carrier gas into a system chamber. While the sample passes through the detection device, a pulsed, high voltage DC spark discharges to form selected charged or energized species within the gas. The spark discharge simultaneously initiates several types of detection systems. For instance, the very short DC spark creates a readily available thermalized electron flux which can be used in a detection system. In an alternate mode of operation, the spark creates a more slowly diffused flux of metastable helium atoms which drift toward selected electrodes within the detector at a controlled rate. The helium atoms will react with molecules of the sample to surrender the excess energy from the excited state to cause sample molecule ionization which, as a secondary and delayed reaction, can be measured by a detection system. Another aspect involves photoionization of gas into positive and negative charged particles normally recombining at high speed. If a select sweep pulse voltage is applied, the recombination is prevented to furnish a signal indicative of the unknown compounds within the gas mixture. Identification and quantification of compounds of interest can, to some extent, be controlled by varying the timing of the spark, the electrode geometry, the voltages of the detector segments, and the modes of interactions observed within the plasma. A complete discussion of the apparatus and basic principles of the measurements are disclosed in detail in U.S. Pat. No. 5,153,519 and are entered herewithin by reference.

While these are success applications for the means and methods disclosed in U.S. Pat. No. 5,153,519 the present disclosure is a remarkable extension to solve many problems. As a first example, the technique provides little control of the compounds within the carrier gas and sample gas mixture which are ionized and therefore detected. If, as an example, it is desired to measure a trace impurity compound in air and both the trace compound and the major constituents of air all are ionized, the relative magnitudes of the major air constituents will introduce serious signal to noise problems thereby degrading the measurement of the desired trace impurity. The teachings disclosed in previously referenced application Ser. No. 08/176,968 present means for not ionizing the major constituents of air, but at the expense of not ionizing, and therefore not detecting, some classes of compounds which may be of interest. In addition, the apparatus disclosed in several of the previously referenced devices are constructed such that the electrodes are exposed to a mixture of carrier and the compound to be detected. Often the compounds of interest are corrosive resulting in corrosion of the discharge electrodes thereby affecting the operation of the measuring system as a function of time. The present invention overcomes the afore mentioned shortcomings of the cited reference devices and also possesses other advantages which will become apparent in the following disclosure.

SUMMARY OF THE INVENTION

The monitoring of trace compounds such as pollutants in gases is of great economic importance. As an example, it might be of interest to monitor commercially produced nitrogen dioxide ($NO_2$) for a trace impurity such as boron triflouride ($BF_3$). Using previously referenced disclosures, it is not possible to use high voltage spark excitation and ionization detection to selectively ionize the trace impurity $BF_3$ without ionizing the $NO_2$. As a second example, it is not possible to used the referenced high voltage spark excitation and ionization detection to selectively ionize pollutant compounds in an atmospheric sample without ionizing the major constituents of air such as nitrogen, oxygen, water and carbon dioxide. Spectroscopic techniques can be used to analyze atomic or molecular emission lines; however, emissions from trace compounds are often masked by emissions from the major constituents of the gas. It is, therefore, highly desirable to ionize only trace pollutants or compounds and to not ionize the major constituents of the sample gas.

Selective ionization of only trace compounds in a gas sample is accomplished by using preferably helium, doped with relatively small concentrations of a selected rare gas, as a carrier gas in the high voltage spark excitation and ionization detector. The percent concentration of the selected dopant in the helium gas is somewhat less than 1.0% and preferably approximately 0.3% to 0.5% range. Helium is excited by the spark discharge creating a relatively slow diffusing flux of metastable helium which drifts downstream from the spark gap. The decay of metastable helium, in turn, excites the dopant gas by a time delayed reaction. The net result is the spark discharge is used to excite the helium-dopant gas mixture which results in the emission of photons arising from the well known resonance lines. In the preferred embodiment, the dopants comprise the rare gases argon (Ar), krypton (Kr), xenon (Xe), or neon (Ne). Only a single type of dopant is used at a given phase of the analysis, although the invention permits the sequential selection from a plurality of dopants as will be detailed in the disclosure which follows. We will first examine a helium-argon carrier gas. The spark discharge is used to excite the helium-argon gas mixture which results in the emission of photons arising from the well known resonance lines of argon at 104.8 and 106.6 nm. An important aspect of the argon emission is that it is used to ionize only impurities in air. The argon resonance lines have energies of 11.62 and 11.83 eV, which are less than the ionization potentials of common components of air such as nitrogen at 15.6 eV, oxygen at 12.08 eV, water at 12.6 eV, and carbon dioxide at 11.8 eV. Argon emission therefore avoids ionizing the major constituents of air while ionizing impurities with ionization potentials less than 11.8 eV. A helium-xenon carrier gas will produce a resonance energy of 9.57 eV which would selectively ionize all compounds with lower ionization potentials. Likewise, helium-krypton will produce resonance energies of 10.64 and 10.03 eV. Helium-neon mixtures will produce a resonance energy of 10.97. By selecting the dopant, the resonance photon can thus be selected thereby providing selective ionization analogous to the previously outlined example involving argon. Using the previously mentioned task of determining trace impurities of $BF_3$ in $NO_2$, a helium-xenon carrier gas is ideally suited in that the ionization potential of $NO_2$ is above the resonance of xenon yet the ionization potentials of $BF_3$ is below the resonance of xenon. Any $BF_3$ impurity is, therefore, selectively ionized while the major constituent $NO_2$ is not ionized. The targeted impurity can be measured with the signal to noise being maximized. The pulsed discharge source is used, with a mixture of helium and selected dopant carrier gas, as a selective photoionization source. This can be applied in a photoionization gas chromatographic detector where the dopant-helium gas mixture is passed through the discharge and the induced dopant radiation passes through the referenced ionization detector until it commingles with and reacts with the analytes, and so that those components with ionization potentials less than the resonance energy of the dopant will become ionized and detected by the electron current generated on the collecting electrode. The magnitude of the current generated on the collecting electrode is indicative of the concentration of the ionized compound. Stated another way, the measure of the collected or "captured" free electrons generated by the ionized compound of interest is a quantitative measure of the concentration of the compound. For brevity, the major apparatus portion of the invention will be referred to as a pulsed capture detector or "PCD".

Argon and other specified emissions can also be used effectively in selective ionization of components being analyzed by ion mobility spectrometry or atmospheric pressure ionization mass spectrometry. In these applications, the positive ions arising from selective photoionization are detected in addition to the collection of electrons. Again, the use of argon radiation is especially important in the ionization of impurities in air.

Emissions from doped carrier gas induced by a high voltage spark are ideally suited for use in an air monitoring device for the detection of pollutants originating from chemical spills or leaks. Quality control in the commercial production of various types of purified gases is another major commercial application of the current invention. The principals of detection are the same as those summarized above and further disclosed, in part, in the referenced parent applications and U.S. patents. Prior art detection has utilized a source external to the gas sample as a source of ionizing radiation for such measurements. Current methods utilize a photoionization lamp containing a window with transparency above approximately 118 nm so that compounds with ionization potentials above approximately 10.5 eV are not ionized. In the current invention, the dopant ionization sources are not external to the sample but, in fact, are created by direct exposure to the discharge and are then commingled with and are in direct contact with the sample. The disclosed invention therefore increases the range of sample ionization from approximately 10.5 eV (the transparency limit of the photoionization lamp) to approximately 11.8 eV (the higher emission of argon). This, in turn, allows gas samples to be selectively analyzed for an expanded number of compounds whose ionization potentials lie within the range of approximately 10.5 to 11.8 eV, yet components not of interest or those which are considered sources of "noise" can be selectively excluded by a judicious choice of dopant gas.

BRIEF DESCRIPTION OF THE DRAWINGS

So that the manner in which the above recited features, advantages and objectives of the present invention are attained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of its scope, for the invention may admit to other equally effective embodiments.

DETAILED DESCRIPTION OF THE PREFERRED EMBODIMENT

The present disclosure is directed to an ionization detector system connected upstream or downstream with existing equipment. The cooperative equipment constitutes one context for ease of explanation. This detector system is devoid of radioactive sources and hence can be used where radioactive materials are limited. Heretofore, it has been common to operate electron capture devices with radioactive material such as a source of ionizing radiation, the most common being tritium and nickel-63.

Figure 1:
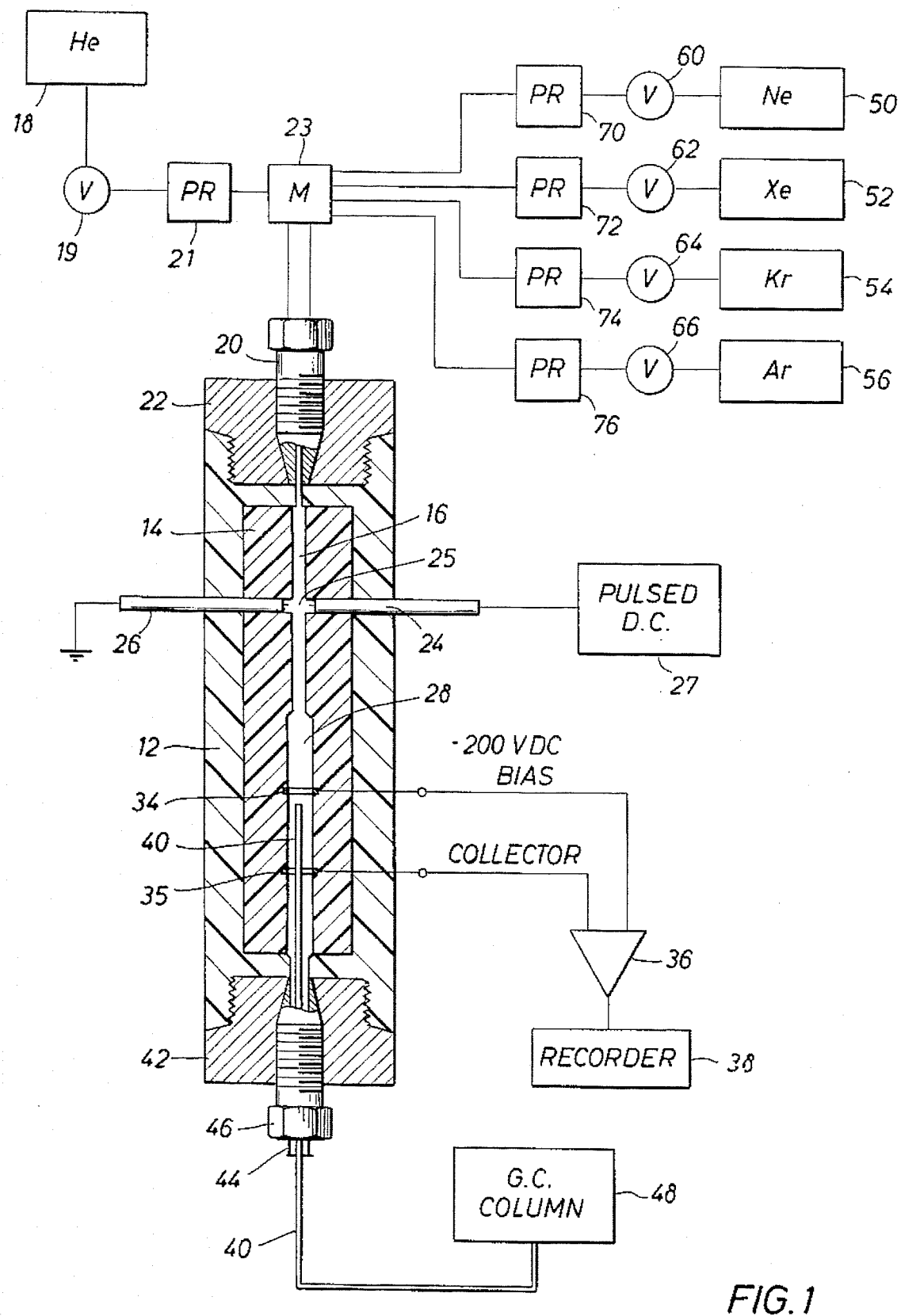
FIG. 1 is a schematic diagram of the detector system showing the detector chamber, the inert and dopant gas supply systems, the sample supply system and a block diagram of the associated electronics.

Referring to FIG. 1, the numeral 10 identifies the detector system of the present invention which will be referred to specifically as the pulsed capture detector or PCD. It is constructed with a long cylindrical housing 12 which contains a cylindrical member 14 which is axially hollow at 16. This forms a passage through which a doped carrier gas is introduced. The preferred carrier gas is helium although other inert gas such as nitrogen can be used. The helium flows from a source 18 through a valve 19 and a regulator 21 to deliver helium at a pressure slightly above atmospheric pressure and flowing at a rate of about 20 to about 150 milliliters per minute. The helium flow is directed to the manifold 23 which is attached to an industry standard fitting 20 formed in a fitting body 22 at the first end of the body 12 of the PCD. By means of a suitable externally threaded nut, the fitting body 22 is held in the illustrated position to assure locking in the ECD apparatus 10. Reservoirs of dopant gas Ne, Xe, Kr and Ar are identified by the numerals 50, 52, 54 and 56, respectively. Reservoirs 50, 52, 54 and 56 are connected through valves and pressure regulators 60 and 70, 62 and 72, 64 and 74, and 66 and 76, respectively, to the manifold 23. The valves 60, 62, 64 and 66 are solenoid operated as is the valve 19. By opening valve 19 and a selected solenoid valve to one of the dopant reservoirs, a carrier gas comprising helium and either Ne, Xe, Kr or Ar is introduced at the manifold 23 and flows directly into the axial passage 16 and moves between the space electrodes 24 and 26.

The electrodes 24 and 26 preferably terminate in facing end faces. More specifically, the facing end faces are constructed on metal rods having a diameter of about 1/16' and which are spaced with end faces approximately 1/16' across passage 16. The faces of the electrodes are preferably flush with the wall of the passage 16. In an optional embodiment, the electrodes are reduced in diameter to a smaller diameter of about 0.3 mm. This can be obtained by forming the two electrodes 24 and 26 of wire stock of that size. In an alternate aspect, larger electrodes can be used and sharpened points can be located so that the spark is traversed to the gas flow in the passage 16. The electrodes 24 and 26 are supported in the cylindrical member 14 which is made of electrically insulating material such as plastic or glass. The terminals of electrodes 24 and 26 are likewise electrically insulated from the body 12 of the PCD which may be made of electrically conducting material such as stainless steel. The electrode 26 is grounded. The electrode 24 is provided with a high voltage pulse of short time duration by the DC source 27 as described in detail in previously referenced U.S. Pat. No. 5,153,519. The two terminals 24 and 26 which form the spark define a sharply fixed, narrowly constrained spark on each spark formation so that the spark does not dance around the two electrode faces, and remains in the form of a straight line. Consequently, it is not otherwise necessary to otherwise confine the spark location.

Figure 2:
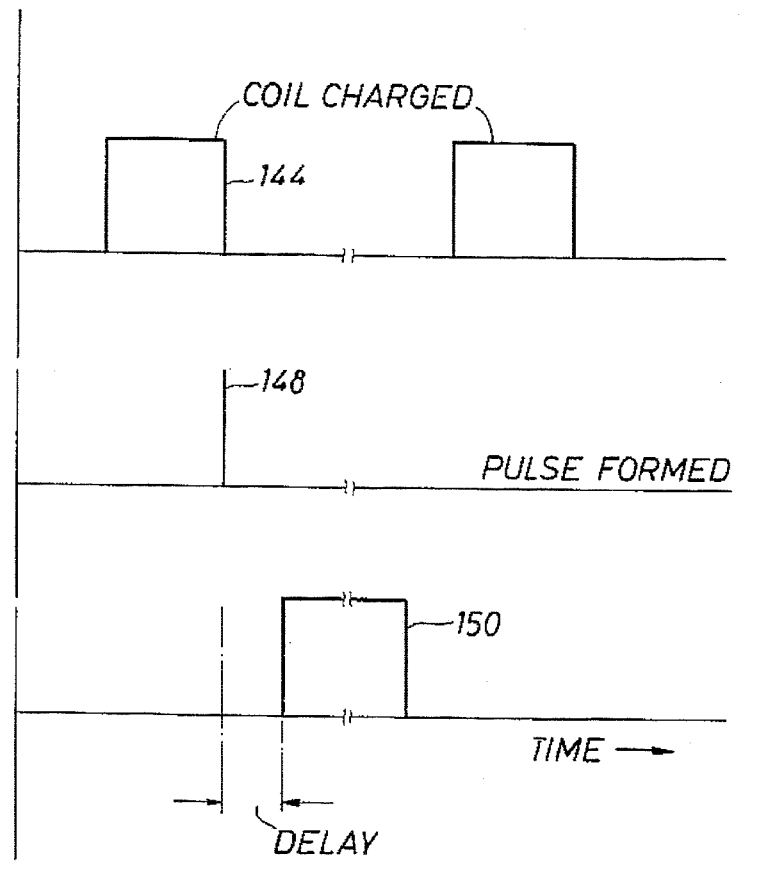
FIG. 2 is a timing chart showing timed relationships of operation of the electronic circuitry depicted in block diagram form in FIG. 1.

FIG. 2 of the drawings depicts several curves which are shown as a function of time. The top curve shows the charging current in the pulse 144 which forms the necessary charge for the operation of the high voltage discharge circuit 143. That circuit forms an output 148 which is a discharge pulse of relatively short duration in time. There is a detection interval which is delayed by a specified time 152, and then a detection pulse is formed at 150.

The flow passage 16 connects downstream with a larger axial hollow passage 28 within cylindrical member 14. Conducting rings 34 and 35 are positioned axially along cylindrical member 14 and are exposed to passage 28. Ring 34 serves as a bias electrode with a bias voltage and also serves as a first terminal for the electrometer 36. The bias can range from about −50 VDC to −400 VDC; bias variation is a scale factor. A bias of −200 VDC is depicted in the drawing of FIG. 2 for purposes of illustration. The second ring 35 is allowed to float and serves as the second terminal for the electrometer 36. The electrometer 36 measures current resulting from the ionization of the trace compounds by the excited dopant component of the carrier gas. The electrometer is input to recorder 38 which yields a record indicative of the magnitude of the ionization current which, in turn, is indicative of the concentration of the trace compound of interest.

The sample gas is input into the passage 28 PCD by way of the capillary or injection tube 40. In the preferred embodiment, sample gas is supplied at a constant flow rate from the gas chromatograph (GC) column 48. The injector tube 40 is preferably coaxially centered within the exhaust or exit passage 44. The exit passage 44 connects with passage 28 through a standard fitting body 42 which, in turn, defines and seals the second end of the body 12 of the PCD.

Doped carrier gas which is introduced into the PCD system flows from top to bottom through the chamber as illustrated in FIG. 1. Sample gas from the GC column 48 enters the passage 28 through the injector tube 40. In this region, the sample gas and the carrier gas containing dopant excited by the spark discharge commingle. Trace compounds within the sample gas are ionized as will be detailed in the following section thereby producing a response of the electrometer 36 which is indicative of the concentration of the trace compound of interest. The carrier gas flow is substantially greater than the sample gas flow from the injector tube 40. After a brief period of commingling and reacting, the mixture of sample and carrier gas is swept from the passage 28 of the PCD chamber and exhausted through the outlet 44.

Attention is now directed toward reactions which take place within the PCD device. Carrier gas mixture comprising an inert gas which is preferably helium and a dopant gas flows into the PCD through inlet fitting 20 and ultimately into the spark gap 25 where ions and atoms in the excited state are formed. In particular, the dopant component of the carrier gas, designated hereafter as "D", is energized and raised to an excited state. The excited dopant passes from the vicinity of spark gap 25 through passage 16 and into the passage 28 of the PCD. Dopant D in the excited state emits photons. Using argon as an example dopant, emission arises from the well known resonance lines of argon at 104.8 and 106.6 nm with corresponding energies of 11.62 and 11.83 eV, respectively. By mixing any of the previously specified dopant gases D with the primary carrier gas such as helium and exciting the carrier gas mixture at the spark gap 25, a source of ionizing radiation, excited dopant (D*), is created along with other components. These other components are detailed in previously referenced U.S. Pat. No. 5,153,519. As the carrier gas containing D* passes from the spark gap 25 through to passage 28, sample gas containing the compound to be measured, referred to as AB for brevity, is commingled with the carrier gas by injection through the tube 40. As a result of this process, the source of ionizing radiation, namely D* which emits the photon $h\gamma_D$, is in the closest proximity to the sample to be ionized and quantified, namely compound AB. Possible reactions that can be induced directly or indirectly by the source D* are:

$$D^* = D + h\gamma_D \tag{1}$$

$$h\gamma_D + AB = AB^+ + e^- + D \tag{2}$$

$$h\gamma_D + AB = A + B^+ + e^- + D \tag{3}$$

$$h\gamma_D + AB = AB^* + D \tag{4}$$

where $AB^* = AB + h\gamma$ $$h\gamma_D + AB = A + B^* + D \tag{5}$$

where $B^* = B + h\gamma$
where $e^-$ denotes a free electron, * denotes an excited state, $h\gamma_D$ denotes photon emission from the excited dopant D*, and $h\gamma$ denotes spectral emission. The equations (4) and (5) describe reactions which form specific and characteristic emission spectra, thereby providing a characteristic signal which enables identification and quantification of the unknown sample compound AB. Spectral analysis can be performed using methods detailed in previously referenced U.S. Pat. No. 5,153,519. Equations (2) and (3) describe reactions which produce free electrons which are the basis of the preferred embodiment of this disclosure. The resulting electron population is measured with electrometer 36, with the measured electron current increasing with increasing concentration of compound AB.

As mentioned previously, the present invention provides means for selecting the type of dopant gas D thereby allowing selected ionization of components of the sample gas. The process will be illustrated by again using Ar as an example of the dopant gas. That is, D=Ar and D*=Ar*. Ar* emits photon radiation at $h\gamma_{Ar}$=11.62 and 11.83 eV. This radiation will not ionize any compound AB with an ionization potential above 11.83 eV. The major components of air are nitrogen with an ionization potential of 15.6 eV, oxygen with an ionization potential of 12.08 eV, water with an ionization potential of 12.6 eV and carbon dioxide with an ionization potential of 13.8 eV. If, therefore, air is the sample gas, the major constituents of air will not be ionized by the Ar* source, but impurities in the air sample such as pollutants with ionization potentials below 11.83 eV will be ionized. Assume also for the purpose of illustration that the sample gas comprises air with traces of impurity AB to be measured which is carbon tetrachloride ($CCl_4$). That is AB=$CCl_4$ in this example. The ionization potential of $CCl_4$ is 11.47 eV therefore $CCl_4$ will be ionized and measured by the system. Developing further a second example mentioned earlier, assume that it is desired to monitor nitrogen dioxide ($NO_2$) sample gas for trace impurities of boron triflouride ($BF_3$) For this measurement, xenon (Xe) is selected as the carrier gas dopant (D=Xe). Xe exhibits a resonance energy at 9.57 eV. The ionization potential of $NO_2$ is 9.75 eV which is above the resonance energy of Kr while the ionization potential of $BF_3$ is 9.25 eV which is below the resonance of Xe. Any $BF_3$ impurity in the $NO_2$ gas will, therefore, be selectively ionized while the major constituent of the sample gas, $NO_2$, will not be ionized. The electrometer 38 will, therefore, respond to any trace concentrations of $BF_3$. It should be noted that neither Ar nor Kr nor Ne would be suitable dopants since the resonance energies of all are greater than the ionization potential of $NO_2$ therefore the $NO_2$ as well as the $BF_3$ would be ionized by reactions involving these dopants.

The pulsed discharge source can therefore be used with a carrier gas mixture of predominantly helium and a relatively small percentage of selected dopants as a selective photoionization source. This can be applied in a photoionization GC detector where the discharge serves as a sample source and the dopant radiation passes through the previously described PCD until it mixes with the analytes coming from the GC column. At this point of mixture within the passage 28, the radiation from the excited dopant is absorbed by the analyte, and those components with ionization potentials less than that of the resonance energy of the selected dopant will become ionized and detected by the electron current generated on the collecting electrode 35 and recorded by the electrometer 36 and recorder 38.

Figure 3:
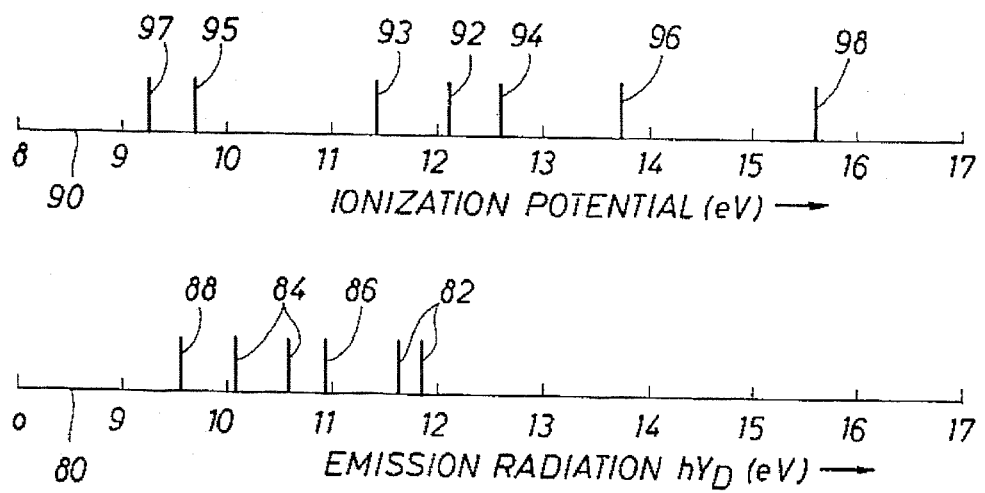
FIG. 3 is a graphical representation of emission photons of the dopants and ionization potentials of compounds used as examples in the disclosure.

FIG. 3 is a graphical representation of the selected ionization concepts discussed above. The axis 80 represents dopant emission radiation $h\gamma_D$ in units of electron volts (eV). The lines identified by the numeral 82 illustrates the Ar emissions at 11.62 and 11.83 eV. The line 86 represents the 10.97 eV emission from Ne and the line 88 represents the 9.57 eV emission from Xe. Finally, emissions at 10.03 and 10.64 from Kr are identified by the numeral 84. Ionization potentials are depicted on the axis 90. The lines identified by the numerals 92, 94, 96 and 98 represent the ionization potentials of the major constituents of air, namely O, $H_2O$, $CO_2$ and N, respectively. The ionization potential of $CCl_4$ used in an example above is identified at 11.47 eV by the numeral 93. Likewise, the ionization potentials of $NO_2$ and $BF_3$ used in a second example are identified by the numerals 95 and 97, respectively. Summarizing the basic concept of the invention in a general manner, for a given dopant emission photon $h\gamma_D$, any element or compound which falls to the high energy side of $h\gamma_D$ (that is, to the right of the emission line as depicted in FIG. 3) will be ionized while any element or compound which falls to the low energy side of $h\gamma_D$ (that is, to the left of the emission line as depicted in FIG. 3) will not be ionized. Dopant gases should, therefore, be selected based upon two criteria which are (1) the ionization potential of the compound of interest to be measured, and (2) the ionization potentials of other constituents of the sample gas which are not to be measured and are, for the purposes of the measurement, considered to generate "noise" in the measure of the compound of interest.

In the actual operation of the invention, selected dopants are introduced into the carrier gas by operating a solenoid valve connected to a reservoir of the selected dopant gas. If, for example, Xe is selected as a dopant, solenoid valve 62 would be opened allowing Xenon gas from the reservoir 52 to flow through the pressure regulator 72 to the manifold 23 where it is commingled with the carrier gas from reservoir 18 prior to entering the PCD chamber through the fitting 2{). Should it be desired to uniquely measure a plurality of compounds within the sample gas, appropriate dopants are introduced into the PCD by operating the corresponding and appropriate solenoid valves. It should be recalled, however, that the previously discussed resonance photon emission and ionization potential criteria must be met in order to obtain optimum measures of the compounds of interest.

The dopant emissions can be used effectively in selective ionization of components being analyzed by ion mobility spectrometry or atmospheric pressure ionization mass spectrometry. In these applications the ions arising from the selective photoionization are detected in addition to the collection of electrons using methods described in detail in referenced U.S. Pat. No. 5,153,519. Again, the use of this radiation is especially important in the ionization of trace impurities in the presence of large concentrations of other constituents, such as the previously described measure of trace pollutants in air.

Argon is especially suited as a dopant in air monitoring devices for the detection of pollutants originating from chemical spills or leaks. The principle of the detector is the same as disclosed previously, where the pollutants are selectively photoionized by the argon resonance emission while the major constituents of air remain neutral thereby greatly increasing the sensitivity of the measurement by increasing the signal-to-noise ratio. Because the source of ionizing radiation from Ar* is mixed within the PCD chamber with the sample being analyzed, a window is not needed in the wall 12 of chamber 10 through which to inject ionizing radiation from an external source. Since a window is not used or needed, compounds with higher ionization potential can be detected than possible with prior art systems. In the prior art, photoionization arises from photons from a photoionization lamp containing a window with transparency above approximately 118 nm so that compounds above approximately 10.5 eV are not ionized and are therefore not detected and analyzed. The current invention now allows the analysis of additional impurity compounds with ionization potentials up to between approximately 10.5 eV and approximately 11.8 eV.

In summary, the preferred embodiment of the disclosure is directed toward, although not limited to, the quantitative analysis of gas samples for trace constituents such as pollutants. Carrier gas dopants can be selected such that compounds to be measured are selectively ionized while other constituents of the sample gas are not ionized. This increases the signal-to-noise ratio of the measurement thereby maximizing accuracy and precision.

While the foregoing disclosure is directed to the preferred embodiments of the present invention, other and further embodiments of the invention may be devised without departing from the basic scope thereof, and the scope thereof is determined by the claims which follow.

What is claimed is:

1. A method for analyzing a sample compound in a carrier gas comprising the steps of:
   (a) commingling a dopant gas and an inert gas forming a carrier gas and the dopant gas is selected such that the resonance energy of said dopant is greater than the ionization energy of said compound to be measured;
   (b) flowing said carrier gas through a chamber for exposure to DC current across the chamber;
   (c) energizing at least one component of said carrier gas to an excited state as a result of exposure to said DC current;
   (d) commingling said carrier gas with a sample gas comprising one or more compounds;
   (e) forming charged particles within said chamber as a result of ionizing radiation emitted in the decay of said excited component of said carrier gas interacting with one or more compounds contained within said sample gas;
   (f) measuring the electrical current resulting from the flow of said charged particles wherein said measurement step occurs in timed relationship to charge dispersal; and
   (g) selectively identifying the concentrations of one or more said compounds contained in said sample utilizing said current measurement.

2. The method of claim 1 wherein said inert gas is helium.

3. The method of claim 2 wherein the resonance energy of said dopant is less than the constituents of the sample gas which are not to be measured.

4. A method for analyzing a sample compound comprising the steps of:
   (a) flowing a carrier gas through a chamber wherein said carrier gas comprises an inert gas and a dopant gas wherein said dopant gas is selected such that the resonance energy of the dopant component is greater than the ionization potential of the compound to be measured in said gaseous sample;
   (b) commingling a gaseous sample with said carrier gas within a chamber forming a composite gas;
   (c) exposing said carrier gas to a spark generated by DC current; and
   (d) optically observing spark caused emissions in said chamber to analyze said gaseous sample component, wherein said emissions involve an energy exchange up to the resonance energy of said dopant.

5. The method of claim 4 wherein said observation is made during DC current flow.

6. The method of claim 4 wherein said observation is made in a region of said chamber not including current flow resulting from the ionization of compounds within said gaseous sample.

7. The method of claim 6 wherein said observed optical emissions are induced by ionizing radiation emitted by said dopant component decaying from a metastable state, said dopant component being excited to a metastable state by said pulsed DC current.

8. A gas detector for identification and quantification of sample compounds, comprising:
   (a) an elongated chamber having a chamber inlet at a first end and an outlet at a second end, and a gas flow path between said inlet and outlet;
   (b) an input manifold for inserting carrier gas into said flow path of said chamber;
   (c) a reservoir, pressure regulator and valve for supplying inert gas at a controlled rate to said manifold;
   (d) a plurality of reservoirs, pressure regulators and valves for selecting one of a plurality of dopants at a controlled rate to said manifold;
   (e) means for introducing into said chamber said inert gas and said selected dopant which are commingled within said manifold thereby forming said carrier gas;
   (f) means for introducing a sample gas into said chamber and commingling said sample gas with said carrier gas;
   (g) two electrodes spaced apart and located to respond to high voltage DC current resulting in sparks within said chamber across said gas flow path and wherein the duration of said sparks minimizes electrode erosion and permits observation of phenomena occurring at and between said sparks and remote from said electrode location;
   (h) means for measuring electrical currents resulting from ions which are produced by said sparks or by metastable species within said carrier gas; and
   (i) means for converting said observed phenomena occurring at and between said sparks and said measured electrical currents to identify and to quantify selected compounds contained within said sample gas.

9. The apparatus of claim 8 wherein said means for measuring said electrical currents comprises a collector and a bias electrode cooperating with an electrometer.

10. The apparatus of claim 8 wherein said means for introducing said sample gas into said chamber comprises an injection tube entering said chamber through a fitting on said second end of said chamber.

11. A method of selectively analyzing a sample of gas for impurities comprising the steps of:
   (a) flowing said carrier gas comprising an inert gas and a selected dopant from a set of at least two dopants through a chamber for exposure to DC current across said chamber thereby energizing molecules of said inert gas to a metastable state;
   (b) energizing said selected dopant to an excited state as a result of the decay of said inert gas metastable molecules;
   (c) commingling a gas sample with said carrier gas within said chamber;
   (d) forming charged particles as a result of ionizing radiation emitted by the decay of said energized dopant component of said carrier gas in said chamber, and wherein the charged particles are formed by selective ionization of impurities of said gas sample based on ionization potentials of said impurities while precluding ionization of major constituents of air; and
   (e) observing reactions induced by ionizing radiation produced by the decay of said excited dopants with said impurities in said gas sample.

12. The method of claim 11 wherein said impurities are identified and quantified by the selected type of dopant and by the measured charged particles resulting from the ionization of impurities produced by ionizing radiation emitted by the decay of said selected excited dopant.

13. The method of claim 11 wherein said impurities are identified and quantified by observing spectral emission of impurities induced by radiation from the decay of said excited dopant.

14. The method of claim 11 wherein said observations are made during said spark discharge.

15. The method of claim 11 wherein said observations are made remote from said spark gap and at a time following said spark discharge.

16. The method of claim 11 wherein impurities with ionization potentials below the resonance radiation from said selected dopant are measured.

17. The method of claim 11 wherein the major constituent of said carrier gas is helium.

18. The method of claim 11 wherein said dopants are rare gases.

19. A method of analyzing an airborne sample comprising the steps of:

(a) providing an airborne sample flowing through a test chamber;

(b) forming a excited species in the chamber characterized by having a ground energy state and excited state of sufficient duration to enable an energy transfer from said excited state of said excited species to the sample; and (c) wherein the excited state causes an energy transfer to a sample constituent wherein the energy range is selected to preclude energizing the constituents of air.

20. The method of claim 19 wherein air constituents of nitrogen, oxygen, water vapor and carbon dioxide are not energized.

21. A method of analyzing a sample compound from a sample compound source such as a GC column comprising the steps of:

(a) through a first inlet, flowing a carrier gas through a chamber for exposure to DC current flowing across the chamber;

(b) energizing at least one component of the carrier gas to an excited state as a result of exposure to said DC current;

(c) flowing the carrier gas through the chamber downstream of the DC current;

(d) introducing a gas sample source gas flow into said chamber through a second inlet downstream from said DC current to thereby commingle the introduced sample flow downstream with the flowing carrier gas;

(e) adjusting the position of introduction downstream;

(f) forming charged particles in the introduced gas sample as a result of the excited state of the carrier gas; and (g) measuring charged particles resultant from commingling of the introduced gas sample flow.

\* \* \* \* \*